US005155037A

United States Patent [19]

Summers

[11] Patent Number: 5,155,037

[45] **Date of Patent: * Oct. 13, 1992**

[54] INSECT SIGNAL SEQUENCES USEFUL TO IMPROVE THE EFFICIENCY OF PROCESSING AND SECRETION OF FOREIGN GENES IN INSECT SYSTEMS

[75] Inventor: Max D. Summers, Bryan, Tex.

[73] Assignee: The Texas A&M University System, College Station, Tex.

[*] Notice: The portion of the term of this patent subsequent to Jun. 11, 2008 has been disclaimed.

[21] Appl. No.: 389,376

[22] Filed: Aug. 4, 1989

[51] Int. Cl.[5] .......................... C12N 5/00; C12N 15/85; C12N 15/87; C07H 15/12

[52] U.S. Cl. .......................... 435/240.2; 435/240.1; 435/320.1; 435/172.3; 435/240.21; 536/27; 935/32; 935/48; 935/70

[58] Field of Search ............... 435/317.1, 320.1, 172.3, 435/252.3, 240.2, 240.21, 240.1, 948, 91; 536/27

[56] References Cited

U.S. PATENT DOCUMENTS

| | | | |
|---|---|---|---|
| 4,394,443 | 7/1983 | Weissman et al. | 435/6 |
| 4,745,051 | 5/1988 | Smith et al. | 435/69.51 |
| 4,879,236 | 11/1989 | Smith et al. | 435/235 |

OTHER PUBLICATIONS

Maeda et al. 1985, Nature 315, 592–594.

Ziegler et al. 1985, Biochem. Biophys. Res. Commun. 133, 337–342.

Schaffer et al. 1986, J. Cell. Biochem. Suppl. 10C, 56, Abs. K6.

Wallace et al. 1981, Nuc. Acids Res. 2, 879–894.

Heijne, et al. 1986 Nuc. Acids Res. 14, 4683–4690.

Baker et al. 1982, in: *Fourth Edition The Study of Biology*, Addison-Wesley Publ. Co., MA., pp. 905 & 907.

Nester et al. 1978, in: *Microbiology* Second Edition, Holt, Rinehart & Winston, New York, pp. 700–701.

Guarino et al. 1986, J. Virol. 57, 563–567.

Guarino et al. 1986, J. Virol. 60, 224–229.

Guarino et al. 1986, J. Virol. 60, 215–223.

Guarino et al. 1987, J. Virol. 61, 2091–2099.

Bradfield and Keeley, Adipokinetic Hormone Gene Sequence from *Manduca sexta, The Journal of Biological Chemistry*, vol. 264, No. 22, pp. 12791–12793 (Aug. 5, 1989).

Schultz-Allen et al., Synthesis of a Homodimer Neurohormone Precursor of Locust Adipokinetic Hormone Studied by In Vitro Translation and cDNA Cloning, *Neuron*, vol. 2 1369–1373 (1989).

M. Snyder, et al., Cuticle Protein Genes of Drosophila: Structure, Organization and Evolution of Four Clustered Genes, *Cell*, vol. 29, 1027–1040 (1982).

R. A. Fisher, et al., HIV infection is blocked in vitro by recombinant soluble CD4, *Nature*, vol. 331, 76–78 (1988).

R. E. Hussey, et al., A soluble CD4 protein selectively inhibits HIV replication and syncytion formation, *Nature*, vol. 331, 78–81 (1988).

P. J. Maddon, et al., The Isolation and Nucleotide Sequence of a cDNA Encoding the T Cell Surface Protein T4: A New Member of the Immunoglobin Gene Family, *Cell*, vol. 42, 93–104 (1985).

Susumu Maeda, Expression of Foreign Genes In Insects Using Baculovirus Vectors, *Ann. Rev. Entomol.*, vol. 34, pp. 351–372 (1989).

(List continued on next page.)

*Primary Examiner*—Robert A. Wax

*Assistant Examiner*—Christopher S. R. Low

*Attorney, Agent, or Firm*—Arnold, White & Durkee

[57] ABSTRACT

The engineering of foreign vertebrate gene constructs by recombinant DNA techniques for the more efficient processing and secretion of foreign genes in insect systems is done by replacing the foreign vertebrate protein signal peptide sequences with protein signal sequences from insect cell secreted proteins. A baculovirus expression vector system is constructed wherein the natural signal DNA peptide sequence associated with the desired foreign gene, such as CD4 (T cell surface protein T4) is replaced by the signal DNA sequence from the insect signal peptides coding for the cuticle gene or adipokinetic hormone.

31 Claims, 3 Drawing Sheets

OTHER PUBLICATIONS

Schaffer et al., Cloning of Adipokinetic Hormone cDNA, *Society for Neuroscience Abstracts,* vol. 14, Part 1, p. 29 (1988).

Schlultz et al., Molecular Biological Studies on the Synthesis of Locust Adipokinetic Hormones, *Society of Neuroscience Abstracts,* vol. 14, Part 1, p. 29 (1988).

Summers and Smith, A Manual of Methods for Baculovirus Vectors and Insect Cell Culture Procedures, Texas Agriculture Experiment Station Bulletin No. 1555, Texas A&M University, College Station, Tex. (1987).

K. Verner & G. Schatz, Protein Translocation Across Membranes, *Science,* vol. 241, 1307–1313 (Sep. 1988).

FIG. 1b

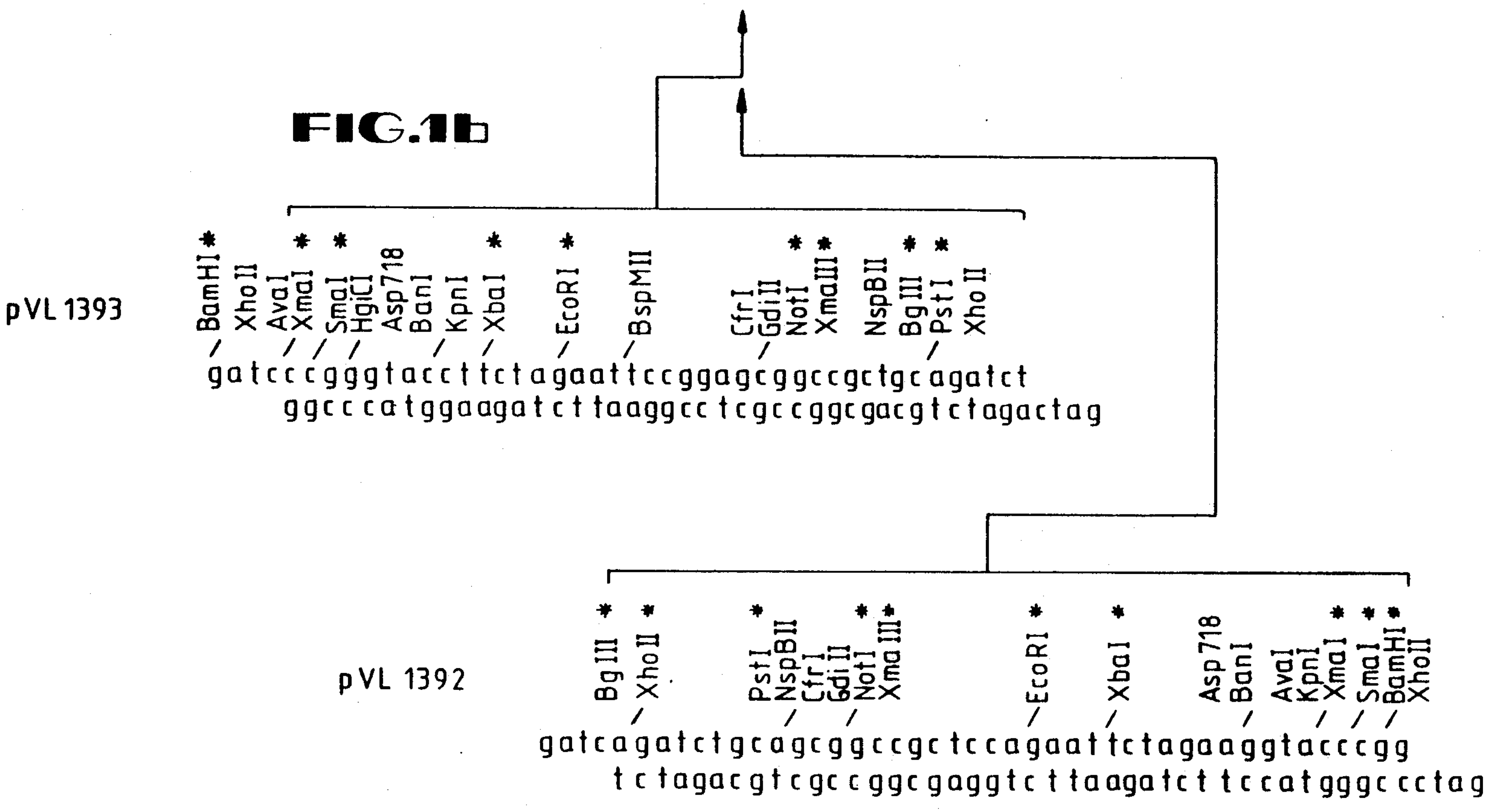

FIG. 1c

LEGEND:

* (INDICATES UNIQUE RESTRICTION SITE)

pVL 1393

BamHI *
XhoII
AvaI
XmaI *
SmaI *
HgiCI
Asp718
BanI
KpnI
XbaI *
EcoRI *
BspMII
CfrI
BglII
NotI *
XmaIII *
NspBII
BglIII *
PstI *
XhoII gatcccggtaccttctagaattccggagcgctgcgtcgacgtctagactag
ggccatggaagatcttaaggcctcgcgacgcagctgcagatct ← ← pVL 1392

BglIII *
XhoII *
PstI *
NspBII
CfrI
BglII
NotI *
XmaIII *
EcoRI *
XbaI *
Asp718
BanI
AvaI
KpnI
XmaI *
SmaI *
BamHI *
XhoII gatcagatctgcagcggccgcggccgctccagaattctagaaggtaccggg
tctagacgtcgccggcgccggcgaggtcttaagatctttccatggccctag

LEGEND:

FIG. 2a

```
BamHI
5'-GATCCATGTTCAAGTTTGTCATGATCTGCGCAGTTTTGGGCCTGGCGGTG-3'
   ---------+---------+---------+---------+---------+------
    3'-GTACAAGTTCAAACAGTACTAGACGCGTCAAAACCCGGACCGCCACCGGTTC-5'
         M  F  K  F  U  M  I  C  A  U  L  G  L  A  U  A (K)
                                                        ↑
                                                  CLEAVAGE SITE
```

FIG. 2b

```
BamHI
5'-GATCCATGTACAAGCTCACAGTCTTCCTGATGTTCATCGCTTTCGTCATCATCGCTGAG-3'
   ---------+---------+---------+---------+---------+---------+----
    3'-GTACATGTTCGAGTGTCAGAAGGACTACAAGTAGCGAAAGCAGTAGTAGCGACTCCGGTTC-5'
         M  Y  K  L  T  U  F  L  M  F  I  A  F  U  I  I  A  E  A (K)
                                                                 ↑
                                                           CLEAVAGE SITE
```

FIG. 2c

```
                                                    RsaI  EcoRI
5'-GCCAAGAAAGTGGTCCTAGGCAAAAAAGGGGATACAGTGGAGTTAACCTGTACG-3'
   ---------+---------+---------+---------+---------+---------+----
      3'-TTTCACCAGGATCCGTTTTTTCCCCTATGTCACCTCAATTGGACATGCTTAA-5'
   (A) K  K  U  U  L  F  K  K  G  D  T  U  E  L  T  C  T
       ↑
CLEAVAGE SITE
```

INSECT SIGNAL SEQUENCES USEFUL TO IMPROVE THE EFFICIENCY OF PROCESSING AND SECRETION OF FOREIGN GENES IN INSECT SYSTEMS

BACKGROUND OF THE INVENTION

A. Field of the Invention

The present invention pertains to the engineering of foreign vertebrate gene constructs by recombinant DNA techniques for the more efficient processing and secretion of foreign genes in insect systems. Particularly, the present invention relates to replacing foreign vertebrate protein signal peptide sequences with protein signal sequences from insect cell secreted proteins.

B. Description of the Related Art

Baculovirus expression vectors (BEVs) have become extremely important tools for the expression of foreign genes, both for basic research and for the production of proteins with direct clinical applications in human and veterinary medicine (W. Doerfler, *Curr. Top. Microbiol. Immunol.,* 131:51-68 (1968); V. A. Luckow and M. D. Summers, *Bio/Technology,* 6:47-55 (1988a); L. K. Miller, *Annual Review of Microbiol.,* 42:177-199 (1988); M. D. Summers, *Curr. Communications in Molecular Biology,* Cold Spring Harbor Press, Cold Spring Harbor, N.Y. (1988)). BEVs are recombinant insect viruses in which the coding sequence for a chosen foreign gene has been inserted behind a baculovirus promoter in place of the viral gene, e.g., polyhedrin (G. E. Smith and M. D. Summers, U.S. Pat. No., 4,745,051, which is incorporated herein by reference).

Several advantages may be enjoyed when employing the BEV system. One of these advantages is the strong polyhedrin promoter which directs a high level of expression of the insert (protein of choice). The newly expressed protein accumulates in large amounts within these infected insect cells. Thus, as a result of the relative strength of the polyhedrin promoter, many different gene inserts can be expressed at very high levels.

Because the polyhedrin gene is a non-essential gene for productive viral infection, another advantage of baculovirus expression vectors is that the recombinants are viable, helper-independent viruses. Also, baculoviruses are noninfectious for vertebrates, and are therefore relatively safe genetic manipulation agents.

Thus, baculoviruses have gained popularity as expression vectors because of the advantages presented above. The BEV system is currently being employed in over 700 laboratories for the overexpression and production of many different gene products. To date, more than 50 different genes have now been expressed by employing this system (V. A. Luckow and M. D. Summers, *Bio/Technology,* 6:47-55 (1988)).

The success of engineering the polyhedrin promoter for the expression of foreign genes is merely a first step indicative of the potential to genetically alter baculoviruses for pest control. Presently there are no reports of a recombinant viral pesticide, but clearly the technology is available and the potential is excellent for inserting foreign genes, encoding for proteins or peptides, which could be highly disruptive to some aspect of insect behavior or metabolism. As mapping of the molecular organization and function of the baculovirus genome and the temporal regulation of these functions is determined, it should be possible to select AcMNPV promoters, in addition to that of polyhedrin, which would be more useful for expressing genes with potential pesticidal activities. To be successful, however, more knowledge is needed of the regulation of baculovirus gene expression, as well as a better understanding of the critical target sites in the insect for such products. (M. D. Summers and G. E. Smith, in: *Genetically Altered Viruses and the Environment,* 319-329, Cold Spring Harbor Laboratory Press (1985) (B. Fields et al. Eds.)).

Theoretically, a highly insect-specific toxin or bioregulator could be expressed under the temporal control of any identified baculovirus promoter which, when expressed, could rapidly debilitate the insect. There are numerous sites for such products within an insect which, if successfully targeted, would increase the pesticidal effectiveness of the baculovirus manyfold. It might be possible to engineer viruses in ways to improve persistence in the environment, to improve virulence, or to expand host range within an acceptable and limited spectrum. With respect to an expanded host range, there are no viral or host factors identified that would allow genetic engineering to proceed on an informed and predictable basis. Basic research on the molecular biology of baculovirus gene function and regulation and the properties of the host insect that play a role in host range and virulence will be essential to develop these potentials and applications. (M. D. Summers and G. E. Smith, in: *Genetically Altered Viruses and the Environment,* 319-329, Cold Spring Harbor Laboratory Press (1985) (B. Fields et al. Eds.)).

There are several families of virus which are insect pathogenic. Particularly useful viruses are from the family Baculoviridae which infect only arthropods, and particularly the Order Lepidoptera. Baculoviruses used for insect control are erratic and slow acting for causing mortality. It has been suggested that a baculovirus be genetically engineered in a way which would disrupt the endocrine balance of the target insect and, therefore, act as a viral pesticide. (G. E. Smith and M. D. Summers, U.S. Pat. No. 4,745,051).

The use of baculovirus vectors relies upon the host cells being derived from Lepidopteran insects. The proteins expressed by the BEVs are, therefore, synthesized, modified and transported in host cells derived from Lepidopteran insects. Most of the genes that have been inserted and produced in the baculovirus expression vector system have been derived from vertebrate species.

Other baculovirus genes in addition to the polyhedrin promoter may be employed to advantage in a baculovirus expression system. These include immediate-early ($\alpha$), delayed-early ($\beta$), late ($\gamma$), or very late ($\delta$), according to the phase of the viral infection during which they are expressed. The expression of these genes occurs sequentially, probably as the result of a "cascade" mechanism of transcriptional regulation. Thus, the immediate-early genes are expressed immediately after infection, in the absence of other viral functions, and one or more of the resulting gene products induces transcription of the delayed-early genes. Some delayed-early gene products, in turn, induce transcription of late genes, and finally, the very late genes are expressed under the control of previously expressed gene products from one or more of the earlier classes. One relatively well-defined component of this regulatory cascade is IE1, a preferred immediate-early gene of *Autographa californica* nuclear polyhedrosis virus (AcMNPV). IE1 is expressed in the absence of other viral functions and encodes a product that stimulates the transcription of several genes of the delayed-early class, including the preferred 39K gene (L. A. Guarino and M. D. Summers, *J. Virol.*, 57:563–571 (1986a); J. Virol.. 61:2091–2099 (1987)), as well as late genes (L. A. Guarino and M. D. Summers, Virol., 162:444–451 (1988)).

Immediate-early genes as described above can be used in combination with a baculovirus gene promoter region of the delayed-early category. Unlike the immediate-early genes, such delayed-early genes require the presence of other viral genes or gene products such as those of the immediate-early genes. The combination of immediate-early genes can be made with any of several delayed-early gene promoter regions such as 39K or one of the delayed-early gene promoters found on the HindIII-k fragment of the baculovirus genome. For example, the 39K promoter region is linked to the heterologous gene of interest and expression is further controlled by the presence of IE1. ((L. A. Guarino and M. D. Summers, *J. Virol.*, 57:563–571 (1986a); *J. Virol.*, 60:215–223 (1986); L. A. Guarino, M. A. Gonzalez and M. D. Summers, J. Virol., 60:224–229 (1986)).

Additionally, when a combination of immediate-early genes with a delayed-early gene promoter region is used, enhancement of the expression of heterologous genes can be realized by the presence of an enhancer sequence in direct cis linkage with the delayed-early gene promoter region. Such enhancer sequences are characterized, by their enhancement of delayed-early gene expression in situations where the immediate-early gene or its product is limited. For example, the hr5 enhancer sequence is linked directly (in cis) to the delayed-early gene promoter region, 39K, thereby enhancing the expression of the cloned heterologous DNA. (L. A. Guarino and M. D. Summers, *J. Virol.*, 57:563–571 (1986a); *J. Virol.*, 60:215–223 (1986b); L. A. Guarino, M. A. Gonzalez and M. D. Summers, *J. Virol.*, 60:224–229 (1986)).

The polyhedrin gene is classified as a very late gene. Therefore, transcription from the polyhedrin promoter requires the previous expression of an unknown, but probably large number of other viral and cellular gene products. In addition to the polyhedrin gene, the p10 genes ("10K genes") of baculoviruses can also be utilized in BEVs. (J. M. Vlak et al., *J. Gen. Virol.*, 69:765:76 (1988)).

Because of this delayed expression of the polyhedrin promoter, state-of-the-art BEVs, such as the exemplary BEV system described by Smith and Summers (U.S. Pat. No. 4,745,051) will express foreign genes only as a result of gene expression from the rest of the viral genome, and only after the viral infection is well underway. This represents a limitation to the use of existing BEVs. The ability of the host cell to process newly synthesized proteins decreases as the baculovirus infection progresses. Thus, gene expression from the polyhedrin promoter occurs at a time when the host cell's ability to process newly synthesized proteins is potentially diminished for certain proteins such as human tissue plasminogen activator. As a consequence, the expression of secretory glycoproteins in BEV systems is complicated due to incomplete secretion of the cloned gene product, thereby trapping the cloned gene product within the cell in an incompletely processed form.

At present, the only mode of achieving secretion of a foreign gene product in insect cells is by way of the foreign gene's native signal peptide. Because the foreign genes are usually from non-insect organisms, their signal sequences may be poorly recognized by insect cells, and hence, levels of expression may be suboptimal.

Heretofore, the efficiency of expression of foreign gene products seems to depend primarily on the characteristics of the foreign protein. On average, nuclear localized or non-structural proteins are most highly expressed, secreted proteins are intermediate, and integral membrane proteins are the least expressed. One factor generally affecting the efficiency of the production of foreign gene products in a heterologous host system is the presence of native signal sequences (also termed presequences, targeting signals, or leader sequences) associated with the foreign gene. The signal sequence is generally coded by a DNA sequence immediately following (5′ to 3′) the translation start site of the desired foreign gene.

The expression dependence on the type of signal sequence associated with a gene product can be represented by the following example: If a foreign gene is inserted at a site downstream from the translational start site of the baculovirus polyhedrin gene so as to produce a fusion protein (containing the N-terminus of the polyhedrin structural gene), the fused gene is highly expressed. But less expression is achieved when a foreign gene is inserted in a baculovirus expression vector immediately following the transcriptional start site and totally replacing the polyhedrin structural gene.

Insertions into the region −50 to −1 significantly alter (reduce) steady state transcription which, in turn, reduces translation of the foreign gene product. Use of the pVL941 vector optimizes transcription of foreign genes to the level of the polyhedrin gene transcription. Even though the transcription of a foreign gene may be optimal, optimal translation may vary because of several factors involving processing: signal peptide recognition, mRNA and ribosome binding, glycosylation, disulfide bond formation, sugar processing, oligomerization, for example.

The properties of the insect signal peptide are expected to be more optimal for the efficiency of the translation process in insect cells than those from vertebrate proteins. This phenomenon can generally be explained by the fact that proteins secreted from cells are synthesized as precursor molecules containing hydrophobic N-terminal signal peptides. The signal peptides direct transport of the select protein to its target membrane and are then cleaved by a peptidase on the membrane, such as the endoplasmic reticulum, when the protein passes through it.

While it has been recognized that the signal sequence associated with a foreign inserted mammalian gene is recognized by the insect cell system and cleaved at the correct sites, the present invention is premised on the use of an insect signal sequence instead of or together with the mammalian signal sequence so as to further enhance the expression of the foreign gene in the insect cell system.

SUMMARY OF THE INVENTION

In general and overall scope, the present invention provides a method for improving the efficiency of expression of foreign gene products in insect systems by replacing the natural signal sequence of the foreign gene with DNA sequences encoding an insect signal peptide.

As disclosed herein, an exemplary insect signal sequence is the sequence encoding for a Lepidopteran adipokinetic hormone (AKH) peptide. The AKH family consists of short blocked neuropeptides that regulate energy substrate mobilization and metabolism in insects. The first structural determination of an AKH was made in 1976 when an AKH common to two locust species was defined. Since then more than a dozen neuropeptides similar to the locust AKH have been recognized. AKH family members from orders as diverse as Orthoptera, Lepidoptera, and Diptera have been described. The AKH family is one of the largest peptide families known. In a preferred embodiment, a DNA sequence coding for a Lepidopteran *Manduca sexta* AKH signal peptide was isolated and cloned. Other insect AKH signal peptides, such as those from the Orthoptera *Schistocerca gregaria* locust can also be employed to advantage.

Another exemplary insect signal sequence is the sequence encoding for Drosophila cuticle proteins such as CP1, CP2, CP3 or CP4. Most of the 9kb region of the Drosophila genome contains genes for the cuticle proteins has been sequenced. Four of the five cuticle genes contains a signal peptide coding sequence interrupted by a short intervening sequence (about 60 base pairs) at a conserved site. Conserved sequences occur in the 5' mRNA untranslated region, in the adjacent 35 base pairs of upstream flanking sequence and at −200 base pairs from the mRNA start position in each of the cuticle genes.

This invention provides a DNA vector useful as an intermediate for the infection or transformation of an insect cell system, said vector containing DNA coding for a baculovirus transcriptional promoter followed downstream by an insect signal DNA sequence capable of directing the secretion of the desired biologically active protein from the insect cell, and a site for the insertion of a foreign gene encoding a biologically active protein, said signal DNA sequence and gene encoding for a biologically active protein under the transcriptional control of a baculovirus promoter.

The vector of the present invention utilizes a baculovirus transcriptional promoter region derived from any of the over 500 baculoviruses generally infecting insects, such as for example the Orders Lepidoptera, Diptera, Orthoptera, Coleoptera and Hymenoptera, including for example but not limited to the viral DNAs of *Autographa californica* MNPV, *Bombyx mori* NPV, *Trichoplusia ni* MNPV, *Rachiplusia ou* MNPV or *Galleria mellonella* MNPV, wherein said baculovirus transcriptional promoter is a baculovirus immediate-early gene IE1 or IEN promoter; an immediate-early gene in combination with a baculovirus delayed-early gene promoter region selected from the group consisting of 39K and a HindIII-k fragment delayed-early gene; or a baculovirus late gene promoter. The immediate-early or delayed-early promoters can be enhanced with transcriptional enhancer elements.

In a preferred embodiment, the insect signal DNA sequence codes for a signal peptide of a Lepidopteran adipokinetic hormone precursor or for an insect signal peptide having substantially a similar chemical composition and function. In a most preferred embodiment, the insect signal DNA codes for a signal peptide of the *Manduca sexta* adipokinetic hormone precurser having the following nucleotide sequence: ATG TAC AAG CTC ACA GTC TTC CTG ATG TTC ATC GCT TTC GTC ATC ATC GCT GAG GCC and allelic variations thereof.

In another preferred embodiment, the insect signal DNA sequence codes for a signal peptide of the Orthoptera *Schistocerca gregaria* locust adipokinetic hormone precurser, or for an insect signal peptide having substantially a similar chemical composition and function, wherein said DNA sequence is further defined as the following nucleotide sequence: ATG GTG CAG CGG TGC CTG CTC CTA GCC TTC CTG GTG GTG GTG GTG GCC CCT GCC CTA TGC TCC GCG and allelic variations thereof.

In another embodiment, the insect signal DNA sequence codes for a signal peptide of the *Drosophila melanogaster* cuticle genes CP1, CP2, CP3 or CP4 or for an insect signal peptide having substantially a similar chemical composition and function.

The present invention further includes the insertion into the above-mentioned vector, of the gene coding for a biologically active protein. In its most preferred embodiment, the desired biologically active protein is CD4 (T Cell Surface Protein T4). According to the preferred embodiment of this invention, CD4 is used as the desired foreign gene product. However, those skilled in the art who have the benefit of this disclosure will recognize that other foreign genes of interest, such as tissue plasminogen activator, human interleukin-2 and human β-interferon, for example, may be used to advantage.

Another embodiment of this invention includes an insect cell system transformed or infected by the above-mentioned vector, said insect cell system being comprised of an insect capable of being infected or transformed, or cell cultures or tissue cultures derived therefrom. In a preferred embodiment, the insect cell system is a Lepidoptera cell line, such as *Spodoptera frugiperda* or *Trichoplusia ni.* The preferred *Spodoptera frugiperda* cell line is the cell line Sf9. According to the preferred embodiment of this invention, the Sf9 cell line is used as the desired host insect cell system. However, those skilled in the art who have the benefit of this disclosure will recognize that other insect cell systems, such as the silkworm *B. mori* may be used to advantage.

In another embodiment, a method of enhanced production of biologically active proteins is disclosed comprising: infecting or transforming the above-mentioned host insect cell systems with a recombinant baculovirus expression vector containing a baculovirus transcriptional promoter followed downstream by an insect signal DNA sequence capable of directing the secretion of the protein from the insect cell and a foreign gene encoding the desired biologically active protein such as CD4, both the insect signal sequence and foreign gene under the transcriptional control of a baculovirus promoter.

BRIEF DESCRIPTION OF THE DRAWINGS

FIG. 1*b*—Depicts a restriction endonuclease map of pVL1393, with its unique restriction sites indicated by asterisks (*). pVL1393 requires the insertion of foreign genes which contain translation initiation signals.

FIG. 1*c*—Depicts a restriction endonuclease map of pVL1392, with its unique restriction sites indicated by asterisks (*). pVL1392 requires the insertion of foreign genes which contain translation initiation signals.

FIG. 2*a*—Depicts Drosophila cuticle gene CP1 leader peptide (Synder et al, 1982, *Cell* 29:1027-1040)

Figure 1A:
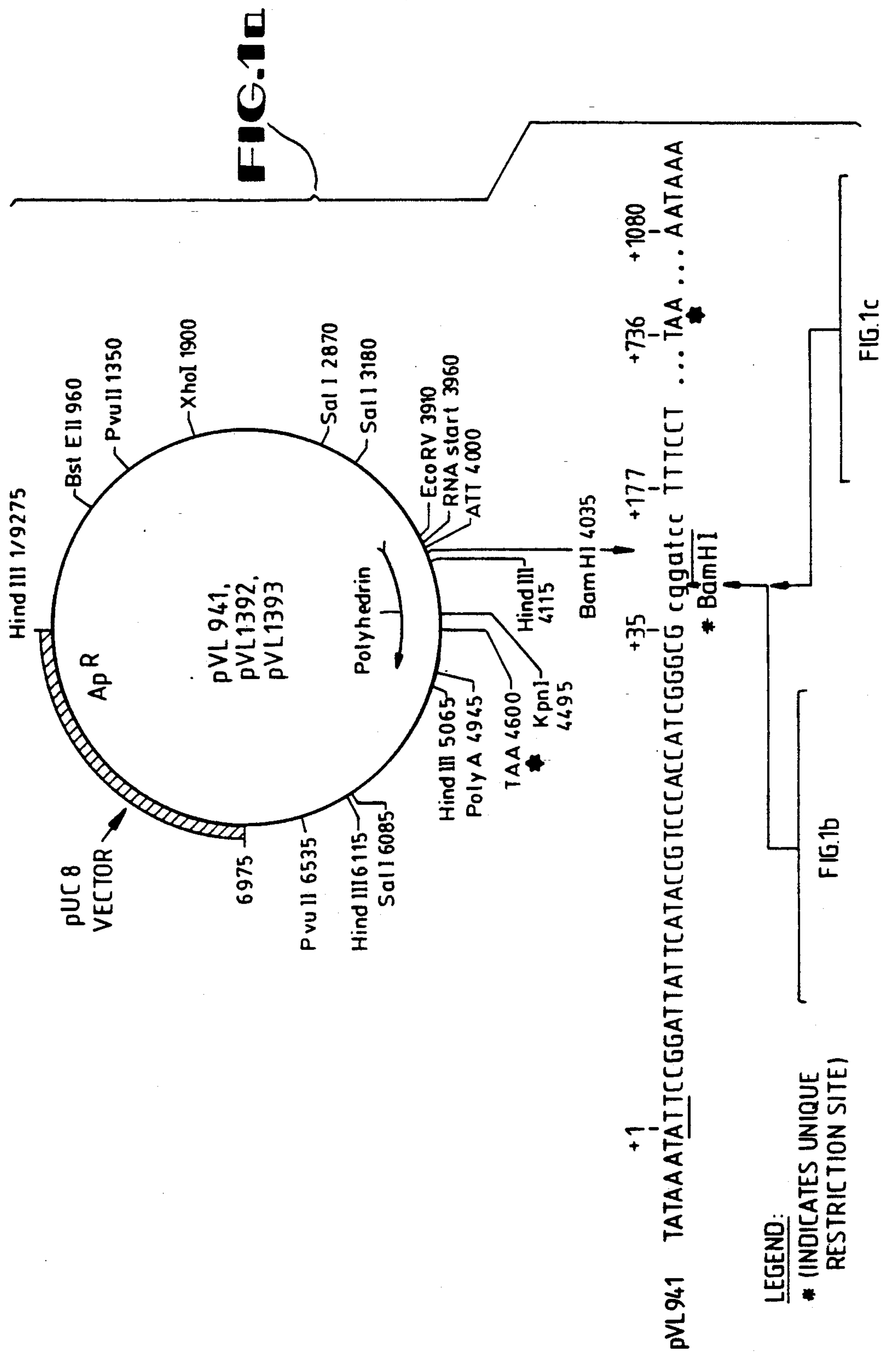
FIG. 1*a*—Depicts a restriction endonuclease map of pVL941, and its unique BamHI restriction site, pVL941 requires the insertion of foreign genes which contain translation initiation signals. pVL941 contains an additional 630 bp EcoRI/Xma III fragment present at position 6975.

and is an example of an oligonucleotide used in the construction of chimeric CD4 expression vectors.

FIG. 2*b*—Depicts Manduca adipokinetic hormone leader peptide and is an example of an oligonucleotide used in the construction of chimeric CD4 expression vectors.

FIG. 2*c*—Depicts amino terminus of mature CD4 peptide (Maddon et al, *Cell* 42:93-103) and is an example of an oligonucleotide used in the construction of chimeric CD4 expression vectors.

DETAILED DESCRIPTION OF THE PREFERRED EMBODIMENTS

Deposit of Plasmids

The preferred transfer vector plasmid pVL941-AKH, containing the AKH signal, plus a coding sequence for the remainder of the AKH precurser was deposited with American Type Culture Collection (Rockville, Md.) on Jul. 27, 1989, and assigned accession number ATCC 40637.

Viral DNA

The baculovirus *Autographa californica* nuclear polyhedrosis virus (AcMNPV), used in the examples as the original source of viral DNA was isolated, according to procedures described in G. E. Smith and M. D. Summers, *Virology,* 89:517-527 (1978) and G. E. Smith and M. D. Summers, *J. Virol.,* 39:125-137 (1981).

According to the preferred embodiment of this invention, a particular strain of AcMNPV, E2, is utilized. However, those skilled in the art who have the benefit of this disclosure will recognize that other baculoviruses and other baculovirus strains may also be suitably utilized to obtain viral DNA. In particular, it is expected that at least the closely related and naturally occurring strains, *Trichoplusia ni* MNPV, *Rachiplusia ou* MNPV, *Galleria mellonella* MNPV and any plaque-purified strains such as the M3, R9, S1 and S3 strains of AcMNPV isolated and characterized in G. E. Smith and M. D. Summers, *J. Virol.,* 33:311-319 (1980), as well as *Bombyx mori* NPV (BmNPV) may be utilized to advantage. Further description of those and other strains are found in G. E. Smith and M. D. Summers, *Virol.,* 89:517-527 (1978).

Plasmid DNA

Plasmids pVL941, pVL1392, pVL1393, were prepared according to the methods described in M. D. Summers and G. E. Smith, *A Manual of Methods for Baculovirus Vectors and Insect Cell Culture Procedures,* Texas Agricultural Experiment Station Bulletin No. 1555, Texas A&M University (1987) ("Bulletin No. 1555"). (See also V. A. Luckow and M. D. Summers, *Virol.,* 170:31-39 (1989)).

The DNA fragment comprising the entire open reading frame of the CD4 (T cell surface protein T4) gene used in the examples was isolated from the plasmid pT4B, which was obtained from Dr. R. Axel, Howard Hughes Medical Institute, Columbia University. See also P. Maddon et al., *Cell,* 42:93-104 (1985).

Insect Cell Lines

The *Spodoptera frugiperda* Sf9 cell line was obtained from American Type Culture Collection (Rockville, Md.) and is assigned accession number ATCC CRL 1711. See M. D. Summers and G. E. Smith, Bulletin No. 1555, supra. Those skilled in the art who have the benefit of this disclosure will recognize that other clonal derivatives of the Sf9 cell line as well as *Trichoplusia ni* and other insects such as the silkworm, *Bombyx mori* , or insect cell cultures derived therefrom can be used to advantage.

Cell Medium

The TNMFH medium used in the examples was prepared according to the methods of M. D. Summers and G. E. Smith, Bulletin No. 1555, supra. (See also W. F. Hink, *Nature,* (London), 226:466-467 (1970)). The fetal calf serum used to supplement the TNMFH medium can be obtained from Hazelton Research Products, Inc. (Lenexa, Kans.).

Methods

Although the methodology described below is believed to contain sufficient detail to enable one skilled in the art to practice the present invention, the plasmids can be constructed and purified using standard recombinant DNA techniques described in T. Maniatis, E. F. Fritsch and J. Sambrook, *Molecular Cloning: A Laboratory Manual,* Cold Spring Harbor Laboratory (1982) under the current regulations described in United States Dept. of HEW, *National Institute of Health (NIH) Guidelines for Recombinant DNA Research.* These references include procedures for the following standard methods: cloning procedures with *E. coli* plasmids, transformation of *E. coli* cells, plasmid DNA purification, phenol extraction of DNA, ethanol precipitation of DNA, agarose gel electrophoresis, purification of DNA fragments from agarose gels, and restriction endonuclease and other DNA-modifying enzyme reactions. Accordingly, these available references are incorporated herein by reference.

The standard methods of insect cell culture, co-transfection and preparation of plasmids in accordance with the examples, are set forth in M. D. Summers and G. E. Smith, *A Manual of Methods for Baculovirus Vectors and Insect Cell Culture Procedures,* Texas Agricultural Experiment Station Bulletin No. 1555, Texas A&M University (1987). This reference also pertains to the standard methods of cloning genes into AcMNPV transfer vectors, plasmid DNA isolation, transferring genes into the AcMNPV genome, viral DNA purification, radiolabelling recombinant proteins and preparation of insect cell culture media. Accordingly, this available reference is incorporated herein by reference.

The procedures for the cultivation of viruses and cells are described in L. E. Volkman and M. D. Summers, *J. Virol,* 19:820-832 (1975) and L. E. Volkman, M. D. Summers and C. H. Hsieh, *J. Virol,* 19:820-832 (1976). Viral growth kinetics were determined as described by L. E. Volkman, et al., supra, using *S. frugiperda* and a 1.5% agarose overlay.

THE INSECT SIGNAL SEQUENCE

The preferred DNA sequence isolated and cloned in the current invention encodes for a Lepidopteran *Manduca sexta* AKH signal peptide which has the following basic sequence:

5' . . . ATG—TAC—AAG—CTC—ACA—GTC—TTC—CTG—ATG—TTC—
Met—Tyr—Lys—Leu—Thr—Val—Phe—Leu—Met—Phe—

-continued

ATC—GCT—TTC—GTC—ATC—ATC—GCT—GAG—GCC . . . 3'
Ile—Ala—Phe—Val—Ile—Ile—Ala—Glu—Ala

Recent evidence confirms that this may very generally be the signal sequence for the other AKH family members. A recent study has found that the signal of AKH in Orthoptera *Schistocerca gregaria* locust has a 22 amino acid signal peptide:

5' . . . ATG—GTG—CAG—CGG—TGC—CTG—CTC—CTA—GCC—TTC—CTG—
Met—Val—Gln—Arg—Cys—Leu—Val—Val—Ala—Leu—Leu—

GTG—GTG—GTG—GTG—GCC—CCT—GCC—CTA—TGC—TCC—GCG . . . 3'
Val—Val—Val—Val—Ala—Ala—Ala—Leu—Cys—Ser—Ala (M. Schultz-Aellen et al., *Neuron,* 2:1369-1373 (1989)). It is believed that within the Order Lepidoptera, the AKH signal displays much greater homology than between other insect orders and therefore all DNA sequences coding for Lepidopteran AKH signal peptides are covered by this invention.

Of course, it is recognized by those, skilled in the art that the DNA sequences may vary due to the degeneracy of the genetic code and codon usage. All DNA sequences which code for the AKH signal peptide amino acid sequences shown in FIGS. 2*a*, 2*b* and 2*c* are included in this invention. Additionally, it will be recognized by those skilled in the art that allelic variations may occur in the DNA sequences which will not significantly change the energy substrate metabolizing activity by the amino acid sequences of the proteins for which the DNA sequences code.

Another exemplary insect signal sequence is the sequence encoding for Drosophila cuticle proteins such as CP1. The larval cuticle protein genes of Drosophila exemplify a set of coordinately expressed genes. Five major urea-soluble cuticle proteins plus a number of minor species are synthesized and secreted by the epidermal cells of late third instar larvae. Genes for three or four of the major third instar cuticle proteins have been found to be clustered in a small (7.9kb) segment of the Drosophila genome, at region 44D on the second chromosome. The genes encoded in this cluster are abundantly expressed in the integument of third instar larvae. Genes for the fifth major cuticle protein and several of the less abundant species lie on the third chromosome. Most of the 9kb region of the Drosophila genome contains genes for the cuticle proteins has been sequenced. Four of the five cuticle genes contains a signal peptide coding sequence interrupted by a short intervening sequence (about 60 base pairs) at a conserved site. Conserved sequences occur in the 5' mRNA untranslated region, in the adjacent 35 base pairs of upstream flanking sequence and at −200 base pairs from the mRNA start position in each of the cuticle genes. (M. Snyder et al., *Cell,* 29:1027-1040 (1982)).

The exemplary insect signal encoding for Diptera *Drosophila melanogaster* cuticle proteins, CP1, CP2, CP3 and CP4, are described in M. Snyder et al., *Cell,* 29:1027-1040 (1982). CP1 has the following basic sequence:

INTRON
−48 V
. . . ATG—TTC—AAG—TTT—GTC—ATG—ATC—TGC—
Met—Phe—Lys—Phe—Val—Met—Ile—Cys—

-continued

GCA—GTT—TTG—GGC—CTG—GCG—GTG—GCC . . .
Ala—Val—Leu—Gly—Leu—Ala—Val—Ala

CP2 has the following basic sequence:

INTRON
−48 V
. . . ATG—TTC—AAG—TTT—GTG—ATG—ATT—CTC—
Met—Phe—Lys—Phe—Val—Met—Ile—Leu—

GCC—GTT—GTG—GGA—GTG—GCT—ACC—GCC . . .
Ala—Val—Val—Gly—Val—Ala—Thr—Ala

CP3 has the following basic sequence:

INTRON
−48 V
. . . ATG—TTC—AAG—ATC—CTG—CTT—GTC—TGT—
Met—Phe—Lys—Ile—Leu—Leu—Val—Cys—

TCT—CTC—GCC—GCC—CTG—GTG—GCC—GCC . . .
Ser—Leu—Ala—Ala—Leu—Val—Ala—Ala

CP4 has the following basic sequence:

INTRON
−48 V
. . . ATG—TTC—AAG—ATC—CTG—CTT—GTC—TGC—
Met—Phe—Lys—Ile—Leu—Leu—Val—Cys—

GCC—CTT—GTC—GCC—CTG—GTG—GCC—GCC . . .
Ala—Leu—Val—Ala—Leu—Val—Ala—Ala (M. Snyder et al., *Cell,* 29:1027-1040 (1982)).

The DNA fragment containing the AKH signal gene can then be subcloned into the appropriate recombinant vector such as a plasmid or viral vector. Those skilled in the art will recognize that there are numerous possible vectors which may be utilized and even more numerous techniques for ligation into these recombinant vectors. The insect virus was a preferred recombinant vector in the current invention, with the baculovirus being most preferred. In the present invention the preferred baculovirus was the *Autographa californica* nuclear polyhedrosis virus, (AcMNPV), strain E2. Alternatively one could use the closely related and naturally occurring strains, *Trichoplusia ni* MNPV, *Rachiplusia ou* MNPV, *Galleria mellonella* MNPV and any plaque-purified strains such as the M3, R9, S1 and S3 strains of AcMNPV isolated and characterized in G. E. Smith and M. D. Summers, *J. Virol.,* 33:311-319 (1980), as well as *Bombyx mori* NPV (BmNPV).

The recombinant vector may then be used to infect or to transform an insect cell system, so that the AKH signal immediately precedes DNA coding for a desired gene product. As used herein, an insect cell system is comprised of an insect capable of being infected or transformed, or cell cultures or tissue cultures derived therefrom. This invention can therefore be employed using the conventional BEV system under the control of baculovirus late promoters, such as polyhedrin or 10K or can be utilized in stably-transformed cells expressing the desired protein product under the control of other baculovirus promoters, such as the IE1 immediate-early promoter or the 39K delayed-early promoter with or without the addition of transcriptional enhancer elements.

EXAMPLE I

Methodology for Insertion of the *Manduca Sexta* Adipokinetic Hormone Precursor Coding Sequence into the *Autographa Californica* Nuclear Polyhedrosis Virus The invention involves the following general strategy: A restriction endonuclease site within the coding region of the gene to be expressed is selected which is downstream from the signal sequence cleavage site. This restriction site links the coding sequence of the mature polypeptide with the insect signal sequence. More particularly, a restriction site which is unique within the open reading frame, is as close as possible to the signal peptidase cleavage site, and produces a 5-prime or 3-prime protruding end is ideal. Two complementary single-stranded oligonucleotides are then synthesized which, when annealed, encode the insect signal sequence and the N-terminal sequence of the mature polypeptide up to the restriction site described above. The addition at the 5-prime end of the synthetic molecule of a sequence which is complementary to the cloning site of the target expression vector facilitates the assembly of the synthetic molecule, vertebrate gene, and expression vector.

A. Construction of Synthetic DNA Encoding the AKH Precursor Signal Peptide Sequence The following steps were utilized for synthesis of double strand DNA representing the signal peptide coding region of the AKH precursor.

1. The following signal peptide-coding, single-strand oligonucleotide was synthesized and purified by standard techniques of oligonucleotide synthesis:

```
5' ATG—TAC—AAG—CTC—ACA—GTC—TTC—CTG—ATG—TTC—ATC—GCT—TTC—
GTC—ATC—ATC—GCT—GAG—GCG 3'
```

2. A 15-oligonucleotide primer complementary to the coding strand was synthesized, and the two oligonucleotides were annealed:

```
5' ATG—TAC—AAG—CTC—ACA—GTC—TTC—CTG—ATG—TTC—
ATC—GCT—TTC—GTC—ATC—ATC—GCT—GAG—GCG 3'
                         3' TAG—TAG—CGA—CTC—CGC 5'
```

3. The strand complementary to the large coding strand was completed enzymatically using the Klenow fragment of DNA polymerase I and deoxynucleoside triphophates:

```
5' ATG—TAC—AAG—CTC—ACA—GTC—TTC—CTG—ATG—TTC—
3' TAC—ATC—TTC—GAG—TGT—CAG—AAG—GAC—TAC—AAG—

ATC—GCT—TTC—GTC—ATC—ATC—GCT—GAG—GCG 3'
TAG—CGA—AAG—CAG—TAG—TAG—CGA—CTC—CGC 5'
```

4. Double strand DNA representing the complete signal peptide was phosphorylated and purified by gel exclusion chromatography:

```
   Met1  Tyr  Lys  Leu  Thr  Val  Phe  Leu  Met  Phe
5' pATG—TAC—AAG—CTC—ACA—GTC—TTC—CTG—ATG—TTC—
3'  TAC—ATC—TTC—GAG—TGT—CAG—AAG—GAC—TAC—AAG—

Ile  Ala  Phe  Val  Ile  Ile  Ala  Glu  Ala19
ATC—GCT—TTC—GTC—ATC—ATC—GCT—GAG—GCG  3'
TAG—CGA—AAG—CAG—TAG—TAG—CGA—CTC—CGCp 5'
```

B. Construction of a Baculovirus Transfer Vector for Expression of Foreign Genes Attached to the AKH Precursor Signal Peptide The strategy for attachment of foreign gene sequences to the AKH precursor signal peptide for baculovirus-directed expression was achieved by way of constructing a pVL941 vector containing the AKH signal code. The vector contains a unique BamHI site for insertion of a foreign gene sequence, wherein such foreign gene sequence has its own ATG translation and initiation codon which is followed by the DNA sequence for the signal peptide sequence for the protein which is to be secreted. In a preferred embodiment of the pVL941 vector, the non-translated leader sequence, −1 to −50 nucleotides is left intact along with a few additional nucleotides between the EcoRV site (approximately −98) and the transcription start (−50). Further the −1 to −8 nontranslated nucleotides need to be retained at the 5' position relative to the translation initiation codon of ATG for any foreign gene being inserted. Similar vectors can be constructed using the pVL1393 and pVL1392 vectors with their respective multiple cassette cloning sites (See FIGS. 1a, 1b, and 1c). The procedure for constructing the signal peptide transfer vector is summarized as follows.

C. Selection and Preparation of Transfer Vector

Of several transfer vectors available for transferring the AKH coding region into AcMNPV genome, the preferred vector pVL941 was utilized because it has proven to result in high level expression of non-fused foreign proteins. A restriction endonuclease map of pVL941 is given in FIG. 1*a*.

The preparation of pVL941 for insertion of the AKH coding region was as follows:

1 μg pVL941 was cleaved at the unique BamHI site:

```
---------GGATCC---------
---------CCTAGG---------
```

(see FIG. 1), by digestion with BamHI. The 5' ends of the cleaved pVL941 were dephosphorylated with calf intestinal phosphatase to prevent recircularization as follows:

```
---------G            + HOGATCC---------
---------CCTAGOH              G---------
```

The two BamHI-cohesive ends were made blunt-ended with deoxynucleotide triphosphates and the Klenow fragment of DNA polymerase I:

```
---------GGATC     + HOGATCC---------
---------CCTAGOH       CTAGG---------
```

The blunt-ended transfer vector was ligated to the double-stranded AKH precursor signal peptide coding region. As a result, this construct has a new unique BamHI site:

```
             Met1 . . . . . . .  Ala19
---------GGATCATG~~~~~~~~GCGGATCC---------
---------CCTAGTAC~~~~~~~~CGCCTAGG---------
                              ↓
                     new unique BamHI site
```

The BamHI-digested, dephosphorylated, blunt-ended pVL941 vector was purified by electrophoresis in agarose gel. By digesting the construct with BamHI, removing the 5' overhanging termini with mung bean nuclease, and dephosphorylating, the construct is ready to accept foreign gene sequences:

```
             Met1 . . . . . . .  Ala19
---------GGATCATG~~~~~~~~GCG//////////////////C---------
---------CCTAGTAC~~~~~~~~CGC//////////////////G---------
. . . . pVL941 . . . . | . AKH signal . . | . . . foreign gene . . . | . . pVL941.
```

al., *Nature,* 331:78-81 (1988)), the amino terminus of the processed CD4 begins with the 26th amino acid of the open reading frame. A unique RsaI site located between amino acids 41 and 43 of the CD4 open reading frame was used to link the carboxy-terminal portion of the CD4 gene with synthetic oligonucleotides encoding an insect signal sequence and amino acids 27-41 of the CD4 precursor.

For two separate exemplary insect signal peptides, the synthetic portion of the chimeric CD4 was constructed as follows: Complementary single-stranded oligonucleotides encoding the Drosophila cuticle gene CP1 leader peptide: ATG TTC AAG TTT GTC ATG ATC TGC GCA GTT TTG GGC CTG GCG GTG GCC (M. Snyder et al., *Cell,* 29:1027-1040 (1982)) or the Manduca adipokinetic hormone leader peptide were synthesized by standard phosphoramidite chemistry. A BamHI cohesive end at the five-prime terminus of each oligonucleotide pair was included for cloning, purposes. Two complementary single-stranded oligonucleotides encoding amino acids 27-42 of the CD4 precursor (including the RsaI site mentioned above) were also synthesized. An EcoRI site was added at the 3-prime end for cloning purposes. The exemplary insect signal oligonucleotides (FIG. 2*a* and 2*b*) were annealed to the synthetic CD4 portion by engineering a six-base overlap between the BamHI and EcoRI digested pUC18. After verifying that the insect sequence was correct by nucleotide sequence analysis, a 100 base pair BamHI-RsaI fragment containing the insect signal sequence and the 5-prime end of the mature CD4 gene was then isolated for each insect signal peptide derivative.

The plasmid pT4B (provided by R. Axel, Howard Hughes Medical Institute, Columbia University) which contains the entire open reading frame of the CD4 gene (P. J. Maddon et al., *Cell,* 42:93-104 (1985)), was then digested with RsaI and XhoII to release a 1.5 kb fragment encoding the carboxy-terminal portion of the CD4 gene. This CD4 fragment and the synthetic fragments described above were ligated in one step into BamHI digested pVL941. Recombinant plasmids containing the CD4 chimeric gene in the proper orientation were identified by restriction mapping. The hybrid signal peptide-CD4 construct after ligation into pVL941 (or pVL1392 or pVL1393 multiple cloning site vectors) were then transferred to the wild-type polyhedrin region after transfection by a double homologous recombination event as described in the conventional BEV procedures of M. D. Summers and G. E. Smith, Bulletin No. 1555, supra.

As disclosed herein, the preferred embodiment of this invention utilizes the Lepidopteran *Manduca sexta* tobacco hornworm adipokinetic hormone peptide leader sequence to enhance the baculovirus promoter controlled expression of foreign proteins in insect cells. However, other insect Order signal peptide leader sequences can be employed to advantage. Specifically, as described above, the Diptera *Drosophila melanogaster* Fruit Fly cuticle genes CP1, CP2, CP3 and CP4 leader sequences, and the Orthoptera *Schistocerca gregaria* locust AKH signal peptide leader sequence, as well as

EXAMPLE II

Construction of CD4 (T Cell Surface Protein T4) Expression Vectors Containing an Insect Signal Peptide In a most preferred embodiment, CD4 (T cell surface protein T4) expression vectors containing an insect signal peptide were constructed. To construct a baculovirus expression vector in which the natural signal peptide of CD4 is replaced with an insect signal sequence, the signal peptide cleavage site on the CD4 precursor must be known. Because sequence data from naturally expressed CD4 in human cells is unavailable, the signal peptide cleavage site derived from recombinant CD4 expressed in vertebrate and insect cells was utilized. For soluble CD4 expressed in Chinese hamster ovary cells (R. A. Fisher et al., *Nature,* 331:76-78 (1988)) and *Spodoptera frugiperda* cells (R. E. Hussey et other insect signal peptide leader sequences can be employed to advantage.

Further modifications of the invention herein disclosed will occur to persons skilled in the art who have the benefit of this disclosure, and all such modifications are deemed to be within the spirit and scope of the invention as defined by the appended claims.

What is claimed is:

1. A Lepidoptera insect cell transformed or infected by an improved DNA vector useful as an intermediate for the infection or transformation of a Lepidoptera insect cell, said vector containing the following operably linked in the order listed: DNA coding for a baculovirus transcriptional promoter followed downstream by an insect signal DNA sequence for directing the secretion of a heterologous protein from the insect cell, and a heterologous foreign gene encoding said heterologous protein, said signal DNA sequence and said gene encoding for said protein being under the transcriptional control of the baculovirus promoter, wherein said baculovirus transcriptional promoter is a baculovirus immediate-early gene IE1 promoter; a baculovirus immediate-early gene IEN promoter; an immediate-early gene in combination with a baculovirus 39K delayed-early gene promoter; an immediate-early gene in combination with a baculovirus HindIII-k delayed-early gene promoter; or a baculovirus late gene promoter.

2. The insect cell of claim 1 wherein the baculovirus transcriptional promoter is from *Autographa californica* MNPV, *Bombyx mori* NPV, *Trichoplusia ni* NMPV, *Rachiplusia ou* MNPV or *Galleria mellonella* MNPV.

3. The insect cell of claim 1 wherein said baculovirus immediate-early or delayed-early gene promoters further include an enhancer, wherein said enhancer is hr1, hr2, hr3, hr4 or hr5.

4. The insect cell of claim 1 wherein said baculovirus late gene promoter is from the baculovirus polyhedrin or 10K gene.

5. The insect cell of claim 1 wherein said insect signal DNA sequence codes for a signal peptide of a Lepidopteran *Manduca sexta* adipokinetic hormone precursor.

6. The insect cell of claim 5 wherein said insect signal DNA codes for a signal peptide of the *Manduca sexta* adipokinetic hormone precursor, having the following nucleotide sequence: ATG TAC AAG CTC ACA GTC TTC CTG ATG TTC ATC GCT TTC GTC ATC ATC GCT GAG GCC.

7. The insect cell of claim 1 wherein said insect signal DNA sequence codes for a signal peptide of the Orthoptera *Schistocerca gregaria* locust adipokinetic hormone precursor, wherein said DNA sequence is further defined as the following nucleotide sequence: ATG GTG CAG CGG TGC CTG CTC CTA GCC TTC CTG GTG GTG GTG GTG GCC CCT GCC CTA TGC TCC GCG.

8. The insect cell of claim 1 wherein said insect signal DNA sequence codes for the signal peptide of the Diptera *Drosophila melanogaster* cuticle genes CP1, CP2, CP3 or CP4;wherein said DNA sequence for the cuticle gene CP1 is further defined as the following nucleotide sequence: ATG TTC AAG TTT GTC ATG ATC TGC GCA GTT TTG GGC CTG GCG GTG GCC; wherein said DNA sequence for the cuticle gene CP2 is further defined as the following nucleotide sequence: ATG TTC AAG TTT GTG ATG ATT CTC GCC GTT GTG GGA GTG GCT ACC GCC; wherein said DNA sequence for the cuticle gene CP3 is further defined as the following nucleotide sequence: ATG TTC AAG ATC CTG CTT GTC TGT TCT CTC GCC GCC CTG GTG GCC GCC; and wherein said DNA sequence for the cuticle gene CP4 is further defined as the following nucleotide sequence: ATG TTC AAG ATC CTG CTT GTC TGC GCC CTT GTC GCC CTG GTG GCC GCC.

9. The insect cell system of claim 1 wherein said heterologous protein is CD4 (T Cell Surface Protein T4).

10. The insect cell of claim 1 wherein said Lepidoptera host cells are *Spodoptera frugiperda, Bombyx mori* or *Trichoplusia ni.*

11. The insect cell system of claim 5 wherein said insect signal DNA codes for a signal peptide of the *Manduca sexta* adipokinetic hormone precursor, having the following amino acid sequence: Met-Tyr-Lys-Leu-Thr-Val-Phe-Leu-Met-Phe-Ile-Ala-Phe-Val-Ile-Ile-Ala-Glu-Ala.

12. The insect cell of claim 1 wherein said insect signal DNA sequence codes for the signal peptide of the Orthoptera *Schistocerca gregaria* locust adipokinetic hormone precursor, wherein said DNA is further defined as the following amino acid sequence: Met-Val-Gln-Arg-Cys-Leu-Val-Val-Ala-Leu-Leu-Val-Val-Val-Val-Ala-Ala-Ala-Leu-Cys-Ser-Ala.

13. The insect cell of claim 1 wherein said insect signal DNA sequence codes for the signal peptide of the Diptera *Drosophila melanogaster* cuticle genes CP1, CP2, CP3 or CP4, wherein said DNA for the cuticle gene CP1 is further defined as encoding the following amino acid sequence: Met-Phe-Lys-Phe-Val-Met-Ile-Cys-Ala-Val-Leu-Gly-Leu-Ala-Val-Ala; wherein said DNA for the cuticle gene CP2 is further defined as encoding the following amino acid sequence: Met-Phe-Lys-Phe-Val-Met-Ile-Leu-Ala-Val-Val-Gly-Val-Ala-Thr-Ala; wherein said DNA for the cuticle gene CP3 is further defined as encoding the following amino acid sequence: Met-Phe-Lys-Ile-Leu-Leu-Val-Cys-Ser-Leu-Ala-Ala-Leu-Val-Ala-Ala; and wherein said DNA for the cuticle gene CP4 is further defined as encoding the following amino acid sequence: Met-Phe-Lys-Ile-Leu-Leu-Val-Cys-Ala-Leu-Val-Ala-Leu-Val-Ala-Ala.

14. The insect cell of claim 1 wherein said heterologous DNA encodes a protein from a vertebrate organism.

15. The insect cell of claim 1 wherein said heterologous DNA encodes a protein from a mammal.

16. An improved DNA vector useful as an intermediate for the infection or transformation of a Lepidoptera insect cell, said vector containing the following operably linked in the order listed: DNA coding for a baculovirus transcriptional promoter followed downstream by an insect signal DNA sequence for directing the secretion of a heterologous protein from the insect cell, and a site for the insertion of a heterologous DNA encoding said heterologous protein, said signal DNA sequence and said site for the insertion of said foreign gene encoding for said protein being under the transcriptional control of said baculovirus promoter, wherein said baculovirus transcriptional promoter is a baculovirus immediate-early gene IE1 promoter; a baculovirus immediate-early gene IEN promoter; an immediate-early gene in combination with a baculovirus 39K delayed-early gene promoter; an immediate-early gene in combination with a baculovirus HindIII-k fragment delayed-early gene promoter; or a baculovirus late gene promoter.

17. The vector of claim 16 wherein the baculovirus transcriptional promoter is from *Autographa californica* MNPV, *Bombyx mori* NPV, *Trichoplusia ni* MNPV, *Rachiplusia ou* MNPV or *Galleria mellonella* MNPV.

18. The vector of claim 16 wherein said baculovirus immediate-early or delayed-early gene promoters further include an enhancer, wherein said enhancer is hr1, hr2, hr3, hr4 or hr5.

19. The vector of claim 16 wherein said baculovirus late gene promoter is from the baculovirus polyhedrin or 10K gene.

20. The vector of claim 16 wherein said insect signal DNA sequence codes for a signal peptide of a Lepidopteran *Manduca sexta* adipokinetic hormone precursor.

21. The vector of claim 20 wherein said insect signal DNA codes for a signal peptide of the *Manduca sexta* adipokinetic hormone precursor, having the following nucleotide sequence: ATG TAC AAG CTC ACA GTC TTC CTG ATG TTC ATC GCT TTC GTC ATC ATC GCT GAG GCC.

22. The vector of claim 16 wherein said insect signal DNA sequence codes for a signal peptide of the Orthoptera *Schistocerca gregaria* locust adipokinetic hormone precursor, wherein said DNA sequence is further defined as the following nucleotide sequence: ATG GTG CAG CGG TGC CTG CTC CTA GCC TTC CTG GTG GTG GTG GTG GCC CCT GCC CTA TGC TCC GCG.

23. The vector of claim 16 wherein said insect signal DNA sequence codes for the signal peptide of the Diptera *Drosophila melanogaster* cuticle genes CP1, CP2, CP3 or CP4, wherein said DNA sequence for the cuticle gene CP1 is further defined as the following nucleotide sequence: ATG TTC AAG TTT GTC ATG ATC TGC GCA GTT TTG GGC CTG GCG GTG GCC; wherein said DNA sequence for the cuticle gene CP2 is further defined as the following nucleotide sequence: ATG TTC AAG TTT GTG ATG ATT CTC GCC GTT GTG GGA GTG GCT ACC GCC; wherein said DNA sequence for the cuticle gene CP3 is further defined as the following nucleotide sequence: ATG TTC AAG ATC CTG CTT GTC TGT TCT CTC GCC GCC CTG GTG GCC GCC; and wherein said DNA sequence for the cuticle gene CP4 is further defined as the following nucleotide sequence: ATG TTC AAG ATC CTG CTT GTC TGC GCC CTT GTC GCC CTG GTG GCC GCC.

24. The vector of claim 16 which further includes the insertion of the heterologous DNA coding for a protein at said insertion site.

25. The vector of claim 16 wherein said heterologous protein is CD4 (T Cell Surface Protein T4).

26. The vector of claim 16 wherein the Lepidoptera host cells are *Spodoptera frugiperda*, *Bombyx mori* or *Trichoplusia ni.*

27. The vector of claim 20 wherein said insect signal DNA codes for a signal peptide of the *Manduca sexta* adipokinetic hormone precursor, having the following amino acid sequence: Met-Tyr-Lys-Leu-Thr-Val-Phe-Leu-Met-Phe-Ile-Ala-Phe-Val-Ile-Ile-Ala-Glu-Ala.

28. The vector of claim 16 wherein said insect signal DNA sequence codes for the signal peptide of the Orthoptera *Schistocerca gregaria* locust adipokinetic hormone precursor, wherein the DNA is further defined as encoding the following amino acid sequence: Met-Val-Gln-Arg-Cys-Leu-Val-Val-Ala-Leu-Leu-Val-Val-Val-Val-Ala-Ala-Ala-Leu-Cys-Ser-Ala.

29. The vector of claim 16 wherein said insect signal DNA sequence codes for the signal peptide of the Diptera *Drosophila melanogaster* cuticle genes CP1, CP2, CP3 or CP4, wherein said DNA for the cuticle gene CP1 is further defined as encoding the following amino acid sequence: Met-Phe-Lys-Phe-Val-Met-Ile-Cys-Ala-Val-Leu-Gly-Leu-Ala-Val-Ala; wherein said DNA for the cuticle gene CP2 is further defined as encoding the following amino acid sequence: Met-Phe-Lys-Phe-Val-Met-Ile-Leu-Ala-Val-Val-Gly-Val-Ala-Thr-Ala; wherein said DNA for the cuticle gene CP3 is further defined as encoding the following amino acid sequence: Met-Phe-Lys-Ile-Leu-Leu-Val-Cys-Ser-Leu-Ala-Ala-Leu-Val-Ala-Ala; and wherein said DNA for the cuticle gene CP4 is further defined as encoding the following amino acid sequence: Met-Phe-Lys-Ile-Leu-Leu-Val-Cys-Ala-Leu-Val-Ala-Leu-Val-Ala-Ala.

30. The vector of claim 16 wherein said heterologous DNA encodes a protein from a vertebrate organism.

31. The vector of claim 16 wherein said heterologous DNA encodes a protein from a mammal.

* * * * *

UNITED STATES PATENT AND TRADEMARK OFFICE

CERTIFICATE OF CORRECTION

PATENT NO. : 5,155,037

DATED : October 13, 1992

INVENTOR(S) : Max D. Summers

It is certified that error appears in the above-indentified patent and that said Letters Patent is hereby corrected as shown below:

In col. 6, line 54, please delete "," (second case) and insert therefor --.--.

In col. 7, line 8, please delete "103" and insert therefor --104--.

In col. 15, line 31, "NMPV" should be --MNPV--.

In col. 16, line 8, please delete "system".

In col. 16, line 24, please insert --encoding-- between "as" and "the".

In col. 16, lines 58 and 59, please delete "foreign gene" and insert therefor --heterologous DNA--.

Signed and Sealed this

Eighth Day of February, 1994

Attest:

BRUCE LEHMAN

*Attesting Officer* *Commissioner of Patents and Trademarks*